(12) United States Patent
He et al.

(10) Patent No.: US 8,664,275 B2
(45) Date of Patent: Mar. 4, 2014

(54) CRYSTALLINE FORM OF BIMATOPROST, PREPARATION METHOD AND USE THEREOF

(75) Inventors: Bingming He, Shanghai (CN); Zhijun Tang, Shanghai (CN); Zhonghao Zhuo, Shanghai (CN); Yunman Zheng, Shanghai (CN); Xiaoliang Gao, Shanghai (CN); Xiaoming Ji, Shanghai (CN)

(73) Assignee: Shanghai Techwell Biopharmaceutical Co., Ltd., Shanghai (CN)

( * ) Notice: Subject to any disclaimer, the term of this patent is extended or adjusted under 35 U.S.C. 154(b) by 0 days.

(21) Appl. No.: 13/505,360

(22) PCT Filed: Jul. 30, 2010

(86) PCT No.: PCT/CN2010/075574
§ 371 (c)(1),
(2), (4) Date: Jul. 16, 2012

(87) PCT Pub. No.: WO2011/050638
PCT Pub. Date: May 5, 2011

(65) Prior Publication Data
US 2012/0270946 A1 Oct. 25, 2012

(30) Foreign Application Priority Data
Nov. 2, 2009 (CN) .......................... 2009 1 0198080

(51) Int. Cl.
*A61K 31/165* (2006.01)
*C07C 235/34* (2006.01)

(52) U.S. Cl.
USPC .......................................... 514/622; 564/171

(58) Field of Classification Search
USPC .......................................... 514/622; 564/171
See application file for complete search history.

(56) References Cited

U.S. PATENT DOCUMENTS

| 5,688,819 A * | 11/1997 | Woodward et al. ........... 514/357 |
| 7,157,590 B2 | 1/2007 | Gutman et al. |
| 7,166,730 B2 | 1/2007 | Gutman et al. |
| 2007/0282006 A1 | 12/2007 | Woodward et al. |
| 2009/0163596 A1 * | 6/2009 | Gutman et al. ............... 514/622 |

FOREIGN PATENT DOCUMENTS

| WO | 2005058812 A2 | 6/2005 |
| WO | 2007111806 A2 | 10/2007 |

OTHER PUBLICATIONS

International Preliminary Report on Patentability for PCT/CN2010/075574 dated May 8, 2012.
Written Opinion of the International Searching Authority for PCT/CN2010/075574 dated Sep. 23, 2010.
International Search Report for PCT/CN2010/075574 dated Sep. 14, 2010.
John K. Haleblian, "Characterization of Habits and Crystalline Modification of Solids and Their Pharmaceutical Applications," Journal of Pharmaceutical Sciences, Aug. 1975, vol. 64, No. 8, pp. 1269-1288.

* cited by examiner

*Primary Examiner* — Rei-tsang Shiao
(74) *Attorney, Agent, or Firm* — Fitch, Even, Tabin & Flannery, LLP (57) ABSTRACT

The crystalline form A of Bimatoprost of formula I, its preparation method and use are provided. There are characteristic peaks where diffraction angles 2θ are 3.2±0.2°, 5.5±0.2°, 11.4±0.2°, 16.7±0.2°, 17.6±0.2°, 19.9±0.2°, 20.8±02° and 22.8±0.2° in the X-ray powder diffraction pattern of the crystalline form A.

19 Claims, 4 Drawing Sheets

Fig. 1

| # | 2-Theta | d(A) | Height | I% |
|---|---|---|---|---|
| 1 | 3.200 | 27.5883 | 5260 | 40.8 |
| 2 | 5.480 | 16.1128 | 5792 | 44.9 |
| 3 | 6.320 | 13.9729 | 742 | 5.7 |
| 4 | 8.340 | 10.5924 | 546 | 4.2 |
| 5 | 9.479 | 9.3225 | 371 | 2.9 |
| 6 | 10.940 | 8.0804 | 2903 | 22.5 |
| 7 | 11.360 | 7.7826 | 4952 | 38.4 |
| 8 | 12.620 | 7.0087 | 729 | 5.6 |
| 9 | 13.760 | 6.4303 | 2258 | 17.5 |
| 10 | 16.720 | 5.2980 | 4202 | 32.6 |
| 11 | 17.600 | 5.0350 | 4095 | 31.7 |
| 12 | 18.420 | 4.8126 | 1880 | 14.6 |
| 13 | 18.979 | 4.6722 | 1128 | 8.7 |
| 14 | 19.880 | 4.4624 | 12556 | 97.3 |
| 15 | 20.780 | 4.2711 | 12905 | 100.0 |
| 16 | 21.660 | 4.0996 | 1526 | 11.8 |
| 17 | 22.820 | 3.8936 | 5015 | 38.9 |
| 18 | 23.940 | 3.7140 | 1559 | 12.1 |
| 19 | 26.160 | 3.4036 | 1395 | 10.8 |
| 20 | 27.680 | 3.2201 | 848 | 6.6 |
| 21 | 28.300 | 3.1509 | 2249 | 17.4 |
| 22 | 30.400 | 2.9379 | 1394 | 10.8 |
| 23 | 32.421 | 2.7592 | 648 | 5.0 |
| 24 | 35.320 | 2.5391 | 688 | 5.3 |

CRYSTALLINE FORM OF BIMATOPROST, PREPARATION METHOD AND USE THEREOF

CROSS REFERENCE TO RELATED APPLICATIONS

This application is a national phase application of International Application No. PCT/CN2010/075574, filed Jul. 30, 2010, claiming priority to Chinese Application No. 200910198080.5, filed Nov. 2, 2009, both of which are incorporated by reference herein in their entirety.

TECHNICAL FIELD

The invention relates to the chemical pharmaceutical field, in particular relates to a new crystalline form of Bimatoprost, a preparation method and use thereof.

BACKGROUND OF THE INVENTION

Figure 1:
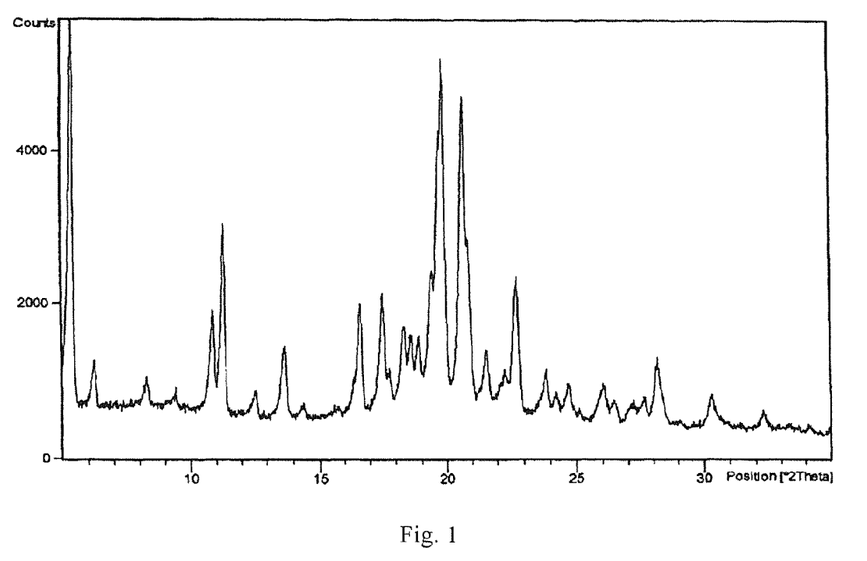
FIG. 1 shows an X-ray powder diffraction pattern of a crystalline form B disclosed in US2009/016359A1.

A PGF2a analogue (Z)-7-[(1R,2R,3R,5S)-3,5-dihydroxyl-2-[(E,3S)-3-hydroxyl-5-phenylpent-1-enyl]cyclopentyl]-N-ethylhept-5-eneamide (Bimatoprost) has been used for reducing intraocular pressure of patients suffering from open-angle glaucoma and ocular hypertension who can not tolerate or are not sensitive enough to other ocular hypotensive agents. Meanwhile, the analogue also has good application prospects in cosmetology. US2007282006A1 has reported that Bimatoprost has the function of promoting growth of eyelashes and hair, and WO2007111806A2 has reported that Bimatoprost has the function of weight reduction. Patents such as U.S. Pat. Nos. 7,166,730B2, 7,157,590B2 and WO2005058812 have detailedly reported a synthesis method of the compound, but research on crystalline forms of the compound has been little reported, and only US2009/016359A1 disclosed a crystalline form (referred to as a crystalline form B, see FIG. 1), the characteristic peaks where diffraction angles 2θ are 5.4, 6.2, 10.9, 11.3, 13.7, 16.6, 17.5, 18.3, 18.6, 18.9, 19.4, 19.7, 19.9, 20.7, 20.9, 21.6, 22.7 and 28.2 in the X-ray powder diffraction (XRPD) pattern of which.

The crystalline form of Bimatoprost in the prior art is insoluble in solvents such as ethyl acetate, tert-butyl acetate, dichloromethane and methyl isobutyl ketone etc. at low temperature, thus when Bimatoprost of the crystal morphology in the prior art is crystallized, it is dissolved at the temperature near the boiling point or boiling temperature of the solvents and then cooled for recrystallization. For example, US2009/016359A1 provided a method for preparing the crystalline form B, wherein the crystalline form B is mainly prepared by dissolving Bimatoprost in a single solvent such as ethyl acetate, tert-butyl acetate, dichloromethane, methyl isobutyl ketone, toluene, acetonitrile, diethyl ether, n-heptane and methyl tertiary butyl ether, or a mixed solvent of these solvents and esters (diethyl ether, methyl tertiary butyl ether and isopropyl ether) at the temperature near the boiling point or boiling temperature, and then cooling for recrystallization. However, it is unfavorable for stability of Bimatoprost, wherein the higher the temperature, the easier the Bimatoprost is degraded, so a method for performing crystallization after dissolution at lower temperature is necessary.

SUMMARY OF THE INVENTION

The invention provides a new crystalline form of Bimatoprost.

The invention provides a preparation method of the new crystalline form of Bimatoprost.

The invention also provides use of the new crystalline form of Bimatoprost.

The invention still provides a pharmaceutical composition containing the new crystalline form of Bimatoprost.

A first aspect of the invention provides a crystalline form A of Bimatoprost, having a structure as shown in formula I, wherein the characteristic peaks at the diffraction angles 2θ are 3.2±0.2°, 19.9±0.2°, 20.8±0.2° and 22.8±0.2° in an X-ray powder diffraction (XRPD) pattern of the crystalline form A;

More preferably, there are further characteristic peaks where diffraction angles 2θ are 5.5±0.2°, 11.4±0.2°, 16.7±0.2° and 17.6±0.2° in the X-ray powder diffraction (XRPD) pattern of the crystalline form A.

More preferably, there are further characteristic peaks where diffraction angles 2θ are 6.3±0.2°, 8.3±0.2°, 9.5±0.2°, 10.9±0.2°, 12.6±0.2°, 13.8±0.2°, 18.4±0.2°, 19.0±0.2°, 21.7±0.2°, 23.930 0.2°, 26.2±0.2°, 27.7±0.2°, 28.3±0.2°, 30.4±0.2°, 32.4±0.2° and 35.3±0.2° in the X-ray powder diffraction (XRPD) pattern of the crystalline form A.

In another preferred example, there are characteristic peaks where diffraction angles 2θ±0.1° are 19.9, 20.8 and 22.8 in the X-ray powder diffraction (XRPD) pattern of the crystalline form A; more preferably, there are further characteristic peaks where diffraction angles 2θ±0.1° are 3.2, 5.5, 11.4, 16.7 and 17.6 in the X-ray powder diffraction (XRPD) pattern of the crystalline form A; and more preferably, there are further characteristic peaks where diffraction angles 2θ±0.1° are 6.3, 8.3, 9.5, 10.9, 12.6, 13.8, 18.4, 19.0, 21.7, 23.9, 26.2, 27.7, 28.3, 30.4, 32.4 and 35.3 in the X-ray powder diffraction (XRPD) pattern of the crystalline form A.

Figure 3:
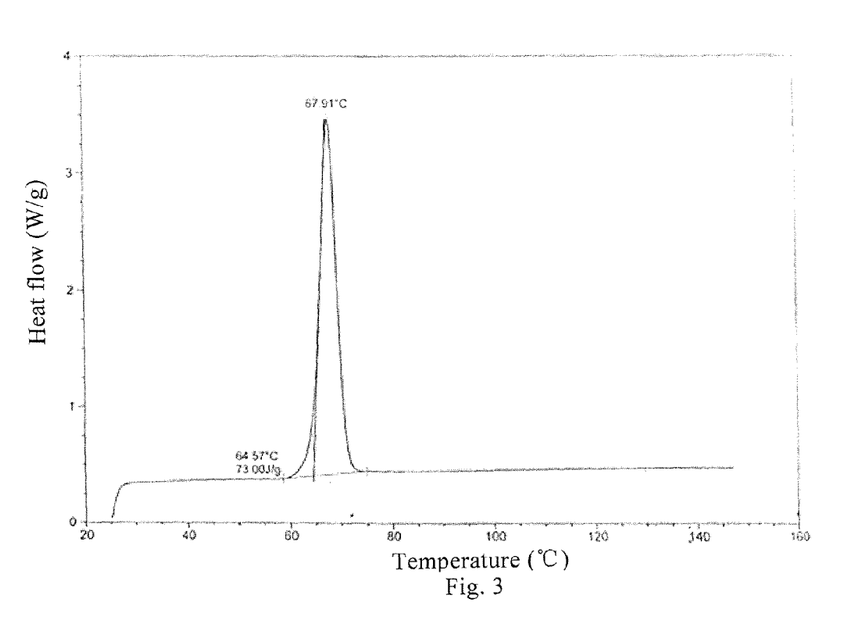
FIG. 3 shows differential scanning calorimetry (DSC) of the crystalline form A of Bimatoprost prepared by the invention.

The crystalline form A of Bimatoprost provided by the invention has the maximum peak value at 66.5-70.5° C. in differential scanning calorimetry (DSC); and more preferably, the crystalline from A has the differential scanning calorimetry (DSC) as shown in FIG. 3.

Figure 4:
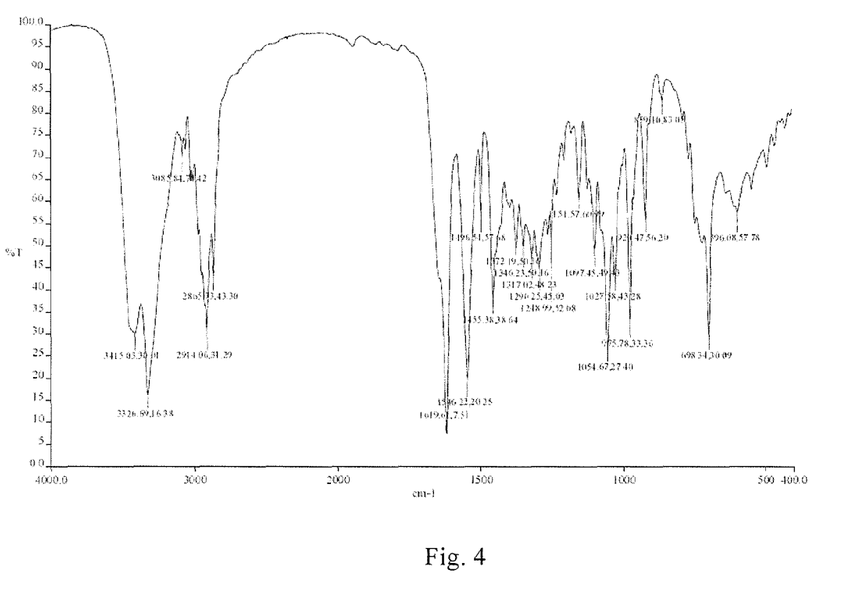
FIG. 4 shows an infrared spectrum of the crystalline form A of Bimatoprost prepared by the invention.

The crystalline form A of Bimatoprost provided by the invention has an infrared spectrum as shown in FIG. 4.

A second aspect of the invention provides a preparation method of the above-mentioned crystalline form A of Bimatoprost provided by the invention, which comprises the steps of:
(1) mixing oily Bimatoprost as shown in formula I with one of the following solvents to obtain solution 1: acetone, butanone, methyl acetate, ethyl acetate, isopropyl acetate, tert-butyl acetate, dichloromethane and isopropanol;
(2) mixing the solution 1 with a non-polar solvent to obtain solution 2; and
(3) stirring the solution 2 to obtain the above-mentioned crystalline form A of Bimatoprost provided by the invention;
wherein the non-polar solvent is selected from one of or a mixture of more of the following: pentane, hexane and petroleum ether.

More preferably, the mixing temperature is 10-30° C. in step (1).

More preferably, the stirring time is 1-50 h in step (2).

More preferably, the stirring temperature is −25° C. to 10° C. in step (3); and more preferably, the stirring temperature is −25° C., −10° C., 0° C., 5° C. or 10° C. in step (3).

More preferably, mixing ratio of a compound Bimatoprost as shown in formula I to the solvent is 1:5-100 to obtain the solution 1 in step (1).

More preferably, mixing ratio of the solution 1 to the non-polar solvent is 0.3-2:1 in step (2).

In another preferred example, the oily Bimatoprost in step (1) is obtained by the following steps: mixing the Bimatoprost as shown in formula I with an alcoholic solvent and then concentrating the mixture to dryness to obtain the oily Bimatoprost; wherein the alcoholic solvent is C1-C4 linear or branched alkyl alcohol.

A third aspect of the invention provides use of the above-mentioned crystalline form A of Bimatoprost provided by the invention for preparing a drug for treating glaucoma.

A fourth aspect of the invention provides a pharmaceutical composition which contains the above-mentioned crystalline form A of Bimatoprost provided by the invention and a pharmaceutically acceptable carrier.

A fifth aspect of the invention provides a preparation method of the above-mentioned pharmaceutical composition provided by the invention, which comprises the step of:

mixing the above-mentioned crystalline form A of Bimatoprost provided by the invention with the pharmaceutically acceptable carrier to obtain the above-mentioned pharmaceutical composition provided by the invention.

The invention hereby provides a new crystal of Bimatoprost which has good stability and can be obtained by dissolution at lower temperature and crystallization.

DETAILED DESCRIPTION OF THE INVENTION

After several trials, the inventors first dissolve Bimatoprost into an alcoholic solvent at lower temperature, then decompress and concentrate at lower temperature to dryness to obtain oily Bimatoprost, then dissolve the oily Bimatoprost into acetone, butanone, methyl acetate, ethyl acetate, isopropyl acetate, tert-butyl acetate, dichloromethane or isopropanol at lower temperature, and finally add a non-polar solvent to cool and separate out crystal. The method avoids the defect of high-temperature dissolution and reduces energy consumption as well.

As used herein, "a compound of formula I" or "Bimatoprost" can used interchangeably and refers to a PGF2a analogue (Z)-7-[(1R,2R,3R,5S)-3,5-dihydroxyl-2-[(E,3S)-3-hydroxyl-5-phenylpent-1-enyl]cyclopentyl]-N-ethylhept-5-eneamide, with the structure as following:

The compound of formula I of the invention refers to Bimatoprost which can be obtained by a method commonly used in the art.

Preparation Method of the Crystalline Form A of Bimatoprost

After thorough study, the inventors found that oily Bimatoprost can be mixed with acetone, butanone, methyl acetate, ethyl acetate, isopropyl acetate, tert-butyl acetate, dichloromethane or isopropanol at lower temperature to form homogeneous solution, then the Bimatoprost solution is diluted by a non-polar solvent such as pentane or hexane or heptane or petroleum ether or a mixture thereof, and then crystallization is performed; and they found by transforming crystallization temperature, molar concentration, cooling rate or stirring conditions, crystallization time, etc., the Bimatoprost is separated out into a single crystalline form A, which further indicates that the crystalline form A is another stable crystalline form. Moreover, the method has high crystallization yield.

Accordingly, the inventors have completed the invention. The invention provides method for preparing the crystalline A form of Bimatoprost, which comprises the following steps:

(1) mixing Bimatoprost as shown in formula I with an alcoholic solvent to obtain solution (2) decompressing and concentrating the solution "a" to dryness to obtain oily Bimatoprost;

(3) mixing the oily Bimatoprost with a polar solvent to obtain solution "b";

(4) mixing the solution "b" with a non-polar solvent to obtain solution "c"; and (5) stirring the solution "c" to obtain the crystalline form A of Bimatoprost provided by the invention;

wherein the Bimatoprost in step (1) is crystalline or amorphous;

wherein, in step (1), the alcoholic solvent is $C_1$-$C_4$ linear or branched alkyl alcohol, preferably methanol, ethanol and isopropanol;

wherein, in step (1), the mixing temperature is 10-30° C., preferably 20-30° C.;

wherein, in step (2), the decompression and concentration temperature is 10-30° C., preferably 20-30° C.;

wherein, in step (3), the polar solvent is selected from one of the following: acetone, butanone, methyl acetate, ethyl acetate, isopropyl acetate, tert-butyl acetate, dichloromethane or isopropanol, preferably acetone, ethyl acetate, dichloromethane or isopropanol;

wherein, in step (3), the mixing temperature is 10-30° C., preferably 20-30° C.;

wherein, in step (3), mixing ratio of the oily Bimatoprost to the polar solvent is 1:5-100 (m:v);

wherein, in step (4), the non-polar solvent is selected from one of the following or a mixture thereof: pentane, hexane, heptane or petroleum ether, preferably n-hexane, n-heptane and petroleum ether;

wherein, in step (4), mixing ratio of the solution "b" to the non-polar solvent is 0.3-2:1 (v:v);

wherein, in step (5), the stirring time is 1-50 h, preferably 10-25 h; and wherein, in step (5), the stirring temperature is −25° C. to 10° C., preferably −10° C. to 5° C.

Once crystallization is fully performed, crystal can be separated by filtration and solvent decantation or other methods, preferably by filtration. Then the crystal can be optionally washed, and dried by a method known in the art.

If the raw material is oily Bimatoprost, it is only necessary to perform operations from step 3. (Refer to Examples 4, 5, 10 and 13 for details).

Identification and Properties of the Crystalline Form A of Bimatoprost

The inventors further study the properties of the crystalline form A of Bimatoprost by many ways and instruments after obtaining the crystalline form A of Bimatoprost.

"X-ray powder diffraction", also known as "X-ray polycrystalline diffraction (XRPD)", is currently a common test method for determining crystal structure (i.e. crystalline forms). A series of diffraction patterns are produced by an X-ray powder diffractometer when X rays penetrate through crystal, and different diffracted rays and intensity thereof in the patterns are determined by atomic groups with a certain structure, thus determining the specific crystalline structure of the crystal.

A method for determining X-ray powder diffraction of crystal is known in the art. For example, a Bruker D8 Advanced X-ray powder diffractometer obtains patterns by copper radiation targets at scanning speed of 2°/min.

Figure 2:
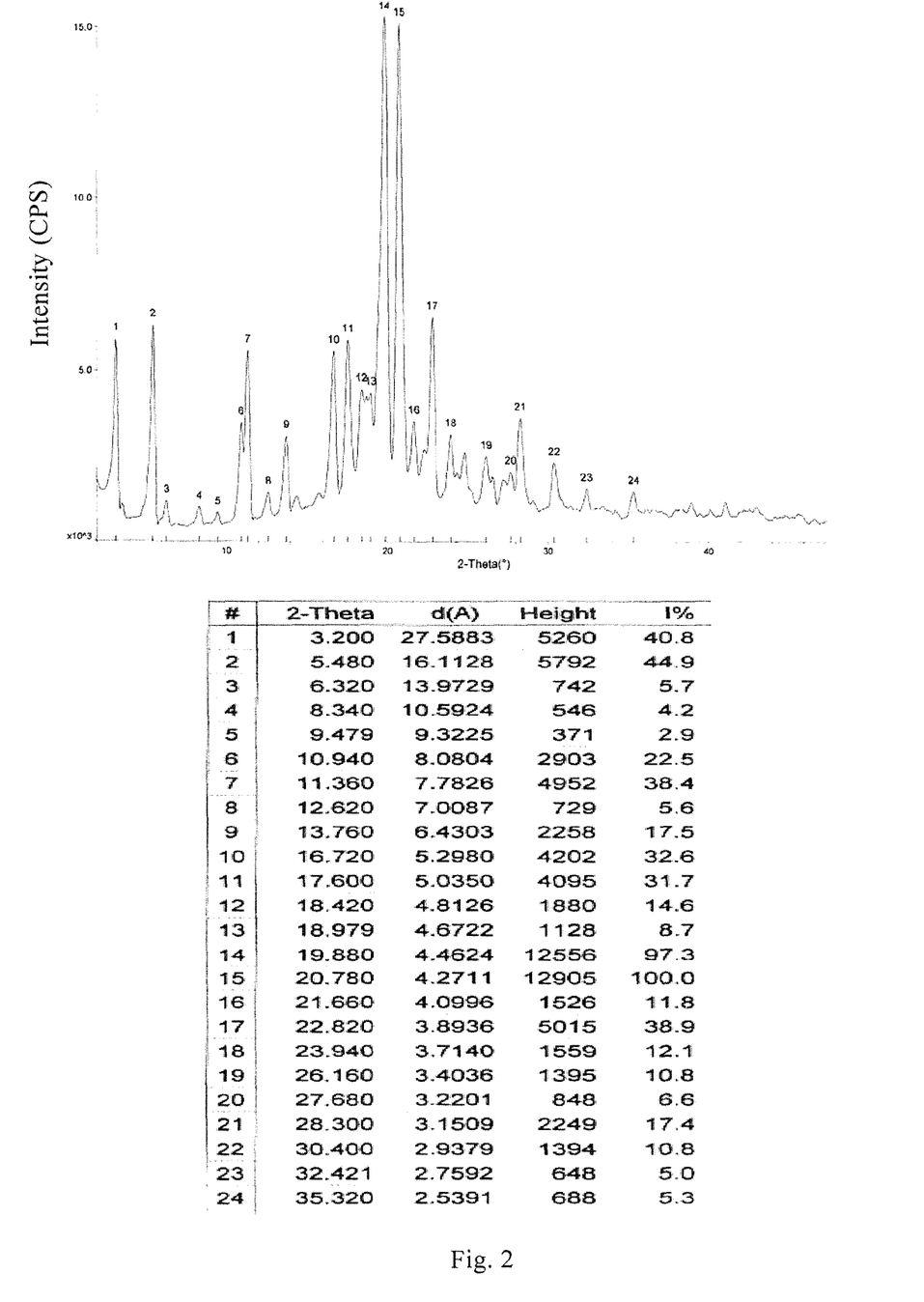
FIG. 2 shows an X-ray powder diffraction pattern of a crystalline form A of Bimatoprost prepared by the invention.

The crystalline form A of Bimatoprost of the invention has specific crystal morphology, and has specific characteristic peaks in an X-ray powder diffraction (XRPD) pattern. In particular, there are characteristic peaks where diffraction angles 2θ are 3.2±0.2°, 19.9±0.2°, 20.8±0.2° and 22.8±0.2° in the X-ray powder diffraction (XRPD) pattern of the crystalline form A of Bimatoprost of the invention; in one preferred embodiment, there are further characteristic peaks where diffraction angles 2θ are 5.5±0.2°, 11.4±0.2°, 16.7±0.2° and 17.6±0.2°; and in another preferred embodiment, there are further characteristic peaks where diffraction angles 2θ are 6.3±0.2°, 8.3±0.2°, 9.5±0.2°, 10.9±0.2°, 12.6±0.2°, 13.8±0.2°, 18.4±0.2°, 19.0±0.2°, 21.7±0.2°, 23.9±0.2°, 26.2±0.2°, 27.7±0.2°, 28.3±0.2°, 30.4±0.2°, 32.4±0.2° and 35.3±0.2°. More preferably, the crystalline form A of Bimatoprost has an X-ray powder diffraction (XRPD) pattern substantially the same as that of FIG. 2.

Peaks at diffraction angles 2θ in the X-ray powder diffraction (XRPD) pattern of the crystalline form A of Bimatoprost of the invention are special characteristic peaks, which are obviously different from the those at diffraction angles 2θ in an X-ray powder diffraction (XRPD) pattern of a crystalline form B reported by US2009/016359A1. Comparison on absorption intensity and angles 2θ of the patterns is as follows: (1) the crystalline form A prepared by the invention has a characteristic peak at diffraction angle 2θ 3.2±0.2° with medium-intensity characteristic absorption while the crystalline form B reported by US2009/016359A1 does not have the same at the diffraction angle 2θ; (2) characteristic peak at the diffraction angle 2θ 5.5±0.2° in the crystalline form A is medium-intensity characteristic absorption while the crystalline form B presents the strongest-intensity characteristic absorption at the same diffraction angle 2θ; (3) the peak with the strongest-intensity characteristic absorption of the crystalline form A is at the diffraction angle 2θ 19.9±0.2° while the peak of crystalline form B is split into three peaks at the diffraction angles 2θ, such as 19.4±0.2°, 19.7±0.2° and 19.9±0.2° and the peaks with the second-strong-intensity characteristic absorption; (4) the peak with the second-strong-intensity characteristic absorption of the crystalline form A is at the diffraction angle 2θ 20.8±0.2° while the peak of crystalline form B is split into two peaks at the diffraction angles 2θ, such as 20.7±0.2° and 20.9±0.2° with the third-strong-intensity characteristic absorption; (5) the peak with the low-intensity characteristic absorption of the crystalline form A is at the diffraction angles 2θ 16.7±0.2° and 17.6±0.2° while the peak of crystalline form B is split into multiple peaks; and (6) the peak with the low-intensity characteristic absorption of the crystalline form A is at the diffraction angles 2θ 30.4±0.2°, 32.4±0.2° and 35.3±0.2° while no peak at the diffraction angle of the crystalline form B.

Differential scanning thermometric analysis, also known as "differential scanning calorimetry (DSC)", is a technology for measuring the relationship between energy difference and temperature of the substance measured and that of reference substance during heating process. The position, shapes and numbers of peaks in DSC patterns are associated with properties of substance, thus the substance can be qualitatively identified. This method is commonly used in the art to detect multiple parameters, such as phase-transition temperature, glass-transition temperature and reaction heat of the substance.

A DSC determination method is known in the art. For example, a DSC Q20 differential scanning calorimeter can be used to obtain DSC scanning patterns of crystal by heating from 25° C. to 300° C. at heating rate of 10° C./min.

In one embodiment of the invention, the maximum peak value is at about 66.5-70.5° C. of the DSC scanning pattern measured for the crystalline form A of Bimatoprost obtained by the method of the invention; preferably, the crystalline form A of Bimatoprost of the invention has a pattern substantially the same as that of FIG. 3; and more preferably, the maximum peak value is at 67.91° C.

Infrared spectroscopy (IR) also can be used to determine crystal structure and its determination method is known in the art. For example, PE Spectrum One B can be used to perform tabletting with the ratio of KBr to samples being 200:1, and scan within the scope of 400-4000 cm$^{-1}$. Infrared spectrogram of the crystalline form A of Bimatoprost of the invention shows characteristic peaks at the following wave number: 3415.03 cm$^{-1}$, 3326.69 cm$^{-1}$, 3085.84 cm$^{-1}$, 2914.06 cm$^{-1}$, 2865.73 cm$^{-1}$, 1619.61 cm$^{-1}$, 1546.22 cm$^{-1}$, 1496.54 cm$^{-1}$, 1455.38 cm$^{-1}$, 1372.19 cm$^{-1}$, 1346.23 cm$^{-1}$, 1317.02 cm$^{-1}$, 1290.25 cm$^{-1}$, 1248.99 cm$^{-1}$, 1151.57 cm$^{-1}$, 1097.45 cm$^{-1}$, 1054.67 cm$^{-1}$, 1027.58 cm$^{-1}$, 975.78 cm$^{-1}$, 920.47 cm$^{-1}$, 859.10 cm$^{-1}$, 698.34 cm$^{-1}$ and 596.08 cm$^{-1}$. Preferably, the crystalline form A has the infrared spectrogram substantially the same as that of FIG. 4.

The crystalline form A of Bimatoprost of the invention has specific stability, which is favorable for storage. The inventors compare the stability of the crystalline form A prepared by the method of the invention with that of the crystalline form B prepared in the prior art by stability test. Data show that the crystalline form A does not degrade while the crystalline form B obviously degrades in case of sealed storage for 4 days at 40° C. Degradation products of the crystalline form B include a compound II and a compound III. This shows that stability of the crystalline form A prepared by the method of the invention is significantly superior to that of the crystalline form B prepared in the prior art.

II

-continued

III

Use of the Crystalline Form A of Bimatoprost and a Composition Thereof.

The crystalline form A of Bimatoprost prepared by the invention has better stability, is easily stored and used and has high purity, thus the crystalline form A can be provided as a pharmaceutical raw material or can be used for preparing a drug for treating glaucoma.

Accordingly, the invention further relates to a composition comprising the crystalline form A of Bimatoprost of the invention, wherein the composition contains an effective amount of the crystalline form A of Bimatoprost, and a pharmaceutically acceptable carrier.

As used herein, the term "containing" or "comprising" includes "comprising", "substantially consisting of" and "consisting of". The term "effective amount" refers to the amount that can produce functions or activity to human and/or animals and is acceptable to human and/or animals.

As used herein, the term "pharmaceutically acceptable" refers to substance that is applicable to human and/or animals without excessive adverse side reactions (e.g. toxicity, stimulation and allergic reaction), i.e. substance with reasonable benefit/risk ratio. The term "pharmaceutically acceptable carrier" refers to carriers for dosing therapeutical agents, including various excipients and diluents. This term refers to some medicament carriers: they are not essential active ingredients in themselves and do not have excessive toxicity after application. Suitable carriers are well known by those ordinary skilled in the art. Full discussion of pharmaceutically acceptable excipients can be found in *Remington's Pharmaceutical Sciences* (Mack Pub. Co., N.J. 1991).

Preferably, the "pharmaceutically acceptable carrier" is selected from a filler, a disintegrant, a lubricant, a flow aid, an effervescent, a flavoring agent, cladding material, an excipient or a sustained/controlled release agent. In a composition, the pharmaceutically acceptable carrier can contain liquid such as water, brine, glycerin and ethanol. Additionally, these carriers may also have adjuvants such as a filler, a disintegrant, a lubricant, a flow aid, an effervescent, a wetting agent or an emulsifier, a flavoring agent and pH buffer substance. Typically, these materials can be formulated in a nontoxic, inert and pharmaceutically acceptable aqueous carrier medium, wherein pH is usually about 5-8, more preferably about 6-8.

The above features mentioned in the invention or features mentioned in the embodiments can be combined in any way. All features disclosed in the specification of the invention can be used along with any composition form, and various features disclosed in the specification can be replaced by alternative features that can provide the same, equivalent or similar purposes. Accordingly, unless otherwise specified, the features disclosed are only general examples of equivalent or similar features.

The main advantages of the invention are as following:
1. A new stable crystal of Bimatoprost is obtained in the invention.
2. The method for preparing the new crystal of Bimatoprost provided by the invention has low energy consumption and stable yield, and is easy for industrialized production.

The invention will be further described below in conjunction with the specific examples. It should be understood that these examples are only used for describing the invention, rather than limiting the scope of the invention. In the following examples, experimental methods of specific conditions are not marked, but the examples are implemented according to normal conditions or conditions suggested by manufacturers. Unless otherwise indicated, all percentages, ratios, proportions or parts are based on weight.

A unit of weight-to-volume percentage (w/v %) in the invention is well known by those skilled in the art. For example, it refers to the weight of a solute in 100 ml solution.

Unless otherwise defined, all professional and scientific terms used herein have the same meaning well-known by those skilled in the art. In addition, any method and material that is similar or equivalent to the recorded content can be used in the method of the invention. More preferred implementation methods and materials as described herein are only used as examples.

As used herein, the term "HPLC purity" refers to the percentage of peak area of the compound as shown in formula I that is subject to HPLC detection and then area normalization according to the obtained chromatogram in the total peak area.

The HPLC detection method is as follows:
Chromatographic column: 4.6×150 mm 3 µm C18 column; column temperature: 35° C.; mobile phase: A: acetonitrile:water (20 mM potassium phosphate buffer solution; pH=2.8) 20:80; B: acetonitrile: water (20 mM potassium phosphate buffer solution; pH=2.8) 40:60; gradient elution conditions: A:B=100: 0, 1 min; A:B=100:0-40:60, 16 min; A:B=40:60, 4 min; A:B=40:60-100:0, 1 min. Flow rate: 1 ml/min; main peak retention time: around 19 mM; sample volume 15 µl; column temperature: 35° C.±5° C.; detection wavelength: 210 nm; running time: 40 min.

EXAMPLE 1

Preparation of Oily Bimatoprost
Oily Bimatoprost is prepared by the synthesis method disclosed in U.S. Pat. No. 7,166,730B2.

EXAMPLE 2

Preparation of the Crystal B of Bimatoprost
The crystalline form B of Bimatoprost is prepared by the method disclosed in US2009/016359A1.

EXAMPLE 3

Preparation of the Crystalline Form a of Bimatoprost
The crystalline form B of Bimatoprost (0.50 g) obtained in Example 2 and methanol (5 ml) were added to a 100 ml eggplant-type flask, dissolved at 10° C., and then decompressed and concentrated at 10° C. to dryness to obtain oily Bimatoprost; acetone (50 ml) was added and heated at 10° C. for dissolution; n-hexane (25 ml) was added dropwise at this temperature, then stirred at −25° C. for 1 h and filtered; and acetone and n-hexane (2:1) at −25° C. were washed for two to three times and dried, thus obtaining 0.46 g crystalline solid. An X-ray powder diffraction pattern is the same as that of FIG. 2, differential scanning calorimetry (DSC) is the same as that of FIG. 3 and infrared spectrogram is the same as that of FIG. 4. (Yield: 92%).

EXAMPLE 4

Preparation of the crystalline form A of Bimatoprost

Oily Bimatoprost (0.50 g) and methyl acetate (25 ml) were added to a 50 ml eggplant-type flask and heated at 30° C. for dissolution; n-hexane (25 ml) was added dropwise at this temperature, cooled to −10° C. under the condition of magnetic stirring, then continuously stirred at this temperature for 5 h and filtered; and methyl acetate and n-hexane (1:1) at −10° C. were washed for two to three times and dried, thus obtaining 0.47 g crystalline solid. An X-ray powder diffraction pattern is the same as that of FIG. 2, differential scanning calorimetry (DSC) is the same as that of FIG. 3 and infrared spectrogram is the same as that of FIG. 4. (Yield: 94%).

EXAMPLE 5

Preparation of the Crystalline Form A of Bimatoprost

Oily Bimatoprost (0.30 g) and dichloromethane (3 ml) were added to a 10 ml eggplant-type flask and heated at 30° C. for dissolution; n-hexane (6 ml) was added dropwise at 30° C. under the condition of magnetic stirring, then cooled to 0° C., continuously stirred for 2 h and filtered; and dichloromethane and n-hexane (1:2) at 0° C. were washed for two to three times and dried, thus obtaining 0.27 g crystalline solid. An X-ray powder diffraction pattern is the same as that of FIG. 2, differential scanning calorimetry (DSC) is the same as that of FIG. 3 and infrared spectrogram is the same as that of FIG. 4. (Yield: 90%).

EXAMPLE 6

Preparation of the Crystalline Form A of Bimatoprost

The crystalline form B of Bimatoprost (0.20 g) obtained in Example 2 and ethanol (4 ml) were added to a 10 ml eggplant-type flask, dissolved at 30° C., and then decompressed and concentrated at 30° C. to dryness to obtain oily Bimatoprost; isopropanol (2 ml) was added and heated at 30° C. for dissolution; n-hexane (6 ml) was added dropwise at 30° C. under the condition of magnetic stirring, then stirred at 0° C. for 50 h and filtered; and isopropanol and n-hexane (1:3) at 0° C. were washed for two to three times and dried, thus obtaining 0.18 g crystalline solid. An X-ray powder diffraction pattern is the same as that of FIG. 2, differential scanning calorimetry (DSC) is the same as that of FIG. 3 and infrared spectrogram is the same as that of FIG. 4. (Yield: 90%).

EXAMPLE 7

Preparation of the Crystalline Form A of Bimatoprost

The crystalline form B of Bimatoprost (0.50 g) obtained in Example 2 and methanol (5 ml) were added to a 50 ml eggplant-type flask, dissolved at 30° C., and then decompressed and concentrated at 30° C. to dryness to obtain oily Bimatoprost; acetone (20 ml) was added and heated at 25° C. for dissolution; n-heptane (10 ml) was added dropwise at 25° C. under the condition of magnetic stirring, then stirred at 10° C. for 25 h and filtered; and acetone and n-heptane (1:1) at 10° C. were washed for two to three times and dried, thus obtaining 0.48 g crystalline solid. An X-ray powder diffraction pattern is the same as that of FIG. 2, differential scanning calorimetry (DSC) is the same as that of FIG. 3 and infrared spectrogram is the same as that of FIG. 4. (Yield: 96%).

EXAMPLE 8

Preparation of the Crystalline Form A of Bimatoprost

The crystalline form B of Bimatoprost (0.20 g) obtained in Example 2 and isopropanol (10 ml) were added to a 50 ml eggplant-type flask, dissolved at 30° C., and then decompressed and concentrated at 30° C. to dryness to obtain oily Bimatoprost; isopropyl acetate (5 ml) was added and heated at 30° C. for dissolution; petroleum ether (10 ml) was added dropwise at 30° C. under the condition of magnetic stirring, then stirred at 5° C. for 40 h and filtered; and isopropyl acetate and petroleum ether (1:2) at 5° C. were washed for two to three times and dried, thus obtaining 0.19 g crystalline solid. An X-ray powder diffraction pattern is the same as that of FIG. 2, differential scanning calorimetry (DSC) is the same as that of FIG. 3 and infrared spectrogram is the same as that of FIG. 4. (Yield: 95%).

EXAMPLE 9

Preparation of the Crystalline Form a of Bimatoprost

The crystalline form B of Bimatoprost (0.50 g) obtained in Example 2 and isopropanol (25 ml) were added to a 100 ml eggplant-type flask, dissolved at 30° C., and then decompressed and concentrated at 30° C. to dryness to obtain oily Bimatoprost; dichloromethane (20 ml) was added and heated at 30° C. for dissolution; petroleum ether (60 ml) was added dropwise at 30° C. under the condition of magnetic stirring, cooled to 10° C., then continuously stirred at this temperature for 10 h and filtered; and dichloromethane and petroleum ether (1:3) at 10° C. were washed for two to three times and dried, thus obtaining 0.48 g crystalline solid. An X-ray powder diffraction pattern is the same as that of FIG. 2, differential scanning calorimetry (DSC) is the same as that of FIG. 3 and infrared spectrogram is the same as that of FIG. 4. (Yield: 96%).

EXAMPLE 10

Preparation of the Crystalline Form A of Bimatoprost

Oily Bimatoprost (0.20 g) and isopropanol (1 ml) were added to a 50 ml eggplant-type flask and heated at 30° C. for dissolution; petroleum ether (3 ml) was added dropwise at this temperature, then stirred at −25° C. for 1 h and filtered; and mixed solution of isopropanol and petroleum ether (1:3) at −25° C. was washed for two to three times and dried, thus obtaining 0.19 g crystalline solid. An X-ray powder diffraction pattern is the same as that of FIG. 2, differential scanning calorimetry (DSC) is the same as that of FIG. 3 and infrared spectrogram is the same as that of FIG. 4. (Yield: 95%).

EXAMPLE 11

Preparation of the Crystalline Form A of Bimatoprost

The crystalline form B of Bimatoprost (0.50 g) obtained in Example 2 and ethanol (10 ml) were added to a 100 ml eggplant-type flask, dissolved at 30° C., and then decompressed and concentrated at 30° C. to dryness to obtain oily Bimatoprost; acetone (50 ml) was added and heated at 20° C. for dissolution; n-hexane (25 ml) was added dropwise at this temperature, then stirred at 0° C. for 10 h and filtered; and mixed solution of acetone and n-hexane (2:1) at 0° C. was washed for two to three times and dried, thus obtaining 0.46 g crystalline solid. An X-ray powder diffraction pattern is the same as that of FIG. 2, differential scanning calorimetry (DSC) is the same as that of FIG. 3 and infrared spectrogram is the same as that of FIG. 4. (Yield: 92%).

EXAMPLE 12

Preparation of the Crystalline Form A of Bimatoprost

The crystalline form B of Bimatoprost (0.20 g) obtained in Example 2 and methanol (1 ml) were added to a 50 ml eggplant-type flask, dissolved at 30° C., and then decompressed and concentrated to dryness to obtain oily Bimatoprost; dichloromethane (5 ml) was added and heated at 30° C. for dissolution; n-hexane (2.5 ml) was added dropwise at this temperature, then cooled to 10° C., and then stirred for 25 h and filtered; and mixed solution of dichloromethane and n-hexane (2:1) at 10° C. was washed for two to three times and dried, thus obtaining 0.18 g crystalline solid. An X-ray powder diffraction pattern is the same as that of FIG. 2, differential scanning calorimetry (DSC) is the same as that of FIG. 3 and infrared spectrogram is the same as that of FIG. 4. (Yield: 90%).

EXAMPLE 13

Preparation of the Crystalline Form A of Bimatoprost

Oily Bimatoprost (0.50 g) and isopropanol (5 ml) were added to a 50 ml eggplant-type flask and heated at 30° C. for dissolution; n-hexane (15 ml) was added dropwise at this temperature, then stirred at 5° C. for 40 h and filtered; and mixed solution of isopropanol and n-hexane (1:3) at 5° C. was washed for two to three times and dried, thus obtaining 0.45 g crystalline solid. An X-ray powder diffraction pattern is the same as that of FIG. 2, differential scanning calorimetry (DSC) is the same as that of FIG. 3 and infrared spectrogram is the same as that of FIG. 4. (Yield: 90%).

EXAMPLE 14

Comparison of Stability

A sample of the crystal A of Bimatoprost prepared by Example 4 was taken (0.8 g; HPLC purity: 99.7%) and divided into 4 parts of equal amount; and the 4 parts were respectively hermetically placed under 40° C. for 1 day, 2 days, 3 days and 4 days and then sampled for analysis, wherein HPLC purity was 99.7%, 99.7%, 99.7% and 99.7% respectively. A sample of the crystal B of Bimatoprost prepared by Example 2 was taken (0.8 g; HPLC purity: 99.6%) and divided into 4 parts of equal amount; and the 4 parts were respectively hermetically placed under 40° C. for 1 day, 2 days, 3 days and 4 days and then sampled for analysis, wherein HPLC purity was 99.4%, 99.2%, 99.1% and 98.7% respectively. The above data shows that the crystalline form A of the invention is more stable than the crystalline form B prepared in the prior art.

The above description is only a more preferred example of the invention, and does not intend to limit the scope of substantial technical contents of the invention. The substantial technical contents of the invention are broadly defined in the scope of claims of the application, and any technical entity or method completed by others shall be considered as being covered within the scope of the claims if it is completely the same or also an equivalent change as defined in the scope of claims of the application.

What is claimed is:

1. A crystalline form A of Bimatoprost, having a structure as shown in formula I, wherein the characteristic peaks at the diffraction angles 2θ are 3.2±0.2°, 19.9±0.2°, 20.8±0.2° and 22.8±0.2° in an X-ray powder diffraction (XRPD) pattern of the crystalline form A:

2. The crystalline form A of Bimatoprost according to claim 1, characterized in that there are further characteristic peaks where diffraction angles 2θ are 5.5±0.2°, 11.4±0.2°, 16.7±0.2° and 17.6±0.2° in the X-ray powder diffraction (XRPD) pattern of the crystalline form A.

3. The crystalline form A of Bimatoprost according to claim 2, characterized in that there are further characteristic peaks where diffraction angles 2θ are 6.3±0.2°, 8.3±0.2°, 9.5±0.2°, 10.9±0.2°, 12.6±0.2°, 13.8±0.2°, 18.4±0.2°, 19.0±0.2°, 21.7±0.2°, 23.9±0.2°, 26.2±0.2°, 27.7±0.2°, 28.3±0.2°, 30.4±0.2°, 32.4±0.2° and 35.3±0.2° in the X-ray powder diffraction (XRPD) pattern of the crystalline form A.

4. The crystalline form A of Bimatoprost according to claim 1, characterized in that there are characteristic peaks where diffraction angles 2θ±0.1° are 19.9, 20.8 and 22.8 in the X-ray powder diffraction (XRPD) pattern of the crystalline form A.

5. The crystalline form A of Bimatoprost according to claim 4, characterized in that 3.2, 5.5, 11.4, 16.7 and 17.6 in the X-ray powder diffraction (XRPD) pattern of the crystalline form A.

6. The crystalline form A of Bimatoprost according to claim 5, characterized in that there are characteristic peaks where diffraction angles 2θ±0.1° are 6.3, 8.3, 9.5, 10.9, 12.6, 13.8, 18.4, 19.0, 21.7, 23.9, 26.2, 27.7, 28.3, 30.4, 32.4 and 35.3 in the X-ray powder diffraction (XRPD) pattern of the crystalline form A.

7. The crystalline form A of Bimatoprost according to claim 1, characterized in that the crystalline form A has the maximum peak value at 66.5-70.5° C. in differential scanning calorimetry (DSC).

8. The crystalline form A of Bimatoprost according to claim 1, characterized in that the crystalline form A has the differential scanning calorimetry (DSC) as shown in FIG. 3.

9. The crystalline form A of Bimatoprost according to claim 1, characterized in that the crystalline form A has an infrared spectrum as shown in FIG. 4.

10. A preparation method of the crystalline form A of Bimatoprost Bimatoprost according to claim 1, characterized in that the method comprises the steps of:
  (1) mixing oily Bimatoprost as shown in formula I with one solvent selected from the following solvents to obtain solution 1: acetone, butanone, methyl acetate, ethyl acetate, isopropyl acetate, tert-butyl acetate, dichloromethane and isopropanol;
  (2) mixing the solution 1 with a non-polar solvent to obtain solution 2; and
  (3) stirring the solution 2 to obtain the crystalline form A of Bimatoprost;
  wherein the non-polar solvent is selected from one of or a mixture of more of the following:
  pentane, hexane, heptane and petroleum ether.

11. The preparation method according to claim 10, characterized in that the mixing temperature is 10-30° C. in step (1).

12. The preparation method according to claim 10, characterized in that the stirring time is 1-50 h in step (2).

13. The preparation method according to claim 10, characterized in that the stirring temperature is −25° C. to 10° C. in step (3).

14. The preparation method according to claim 13, characterized in that the stirring temperature is −25° C., −10° C., 0° C., 5° C. or 10° C. in step (3).

15. The preparation method according to claim 10, characterized in that the mixing ratio of a compound Bimatoprost as shown in formula I to the solvent is 1:5-100 to obtain the solution 1 in step (1).

16. The preparation method according to claim 10, characterized in that the mixing ratio of the solution 1 to the non-polar solvent is 0.3-2:1 in step (2).

17. The preparation method according to claim 10, characterized in that the oily Bimatoprost in step (1) is obtained by the following steps: mixing the Bimatoprost as shown in formula I with an alcoholic solvent and then concentrating the mixture to dryness to obtain the oily Bimatoprost; wherein the alcoholic solvent is C1-C4 linear or branched alkyl alcohol.

18. A method of treating glaucoma comprising the step of:
    administering a pharmaceutical composition including the crystalline form A of Bimatoprost according to claim 1 combined with a pharmaceutically acceptable carrier in an amount effective for treating glaucoma.

19. A preparation method of a pharmaceutical composition, characterized in that the method comprises the step of:
    mixing the crystalline form A of Bimatoprost according to claim 1 with a pharmaceutically acceptable carrier to obtain a pharmaceutical composition.

\* \* \* \* \*